(12) United States Patent
Mehra et al.

(10) Patent No.: US 12,308,140 B2
(45) Date of Patent: May 20, 2025

(54) ADDITIVELY MANUFACTURED CABLE GLAND

(71) Applicant: Eaton Intelligent Power Limited, Dublin (IE)

(72) Inventors: Rhythm Mehra, Amritsar (IN); Himanshu Gangadhar Khokle, Nagpur (IN); Jayram Shivajirao Desai, Kolhapur (IN)

(73) Assignee: EATON INTELLIGENT POWER LIMITED, Dublin (IE)

( * ) Notice: Subject to any disclaimer, the term of this patent is extended or adjusted under 35 U.S.C. 154(b) by 132 days.

(21) Appl. No.: 17/645,502

(22) Filed: Dec. 22, 2021

(65) Prior Publication Data

US 2022/0208419 A1  Jun. 30, 2022

Related U.S. Application Data

(60) Provisional application No. 63/131,866, filed on Dec. 30, 2020.

(51) Int. Cl.
| | | |
|---|---|---|
| *H01B 17/58* | (2006.01) | |
| *A61K 31/5025* | (2006.01) | |
| *A61K 47/10* | (2017.01) | |
| *A61K 47/32* | (2006.01) | |
| *A61K 47/38* | (2006.01) | |
| *B33Y 80/00* | (2015.01) | |
| *H02G 15/02* | (2006.01) | |

(52) U.S. Cl.
CPC ......... *H01B 17/58* (2013.01); *A61K 31/5025* (2013.01); *A61K 47/10* (2013.01); *A61K 47/32* (2013.01); *A61K 47/38* (2013.01); *B33Y 80/00* (2014.12); *H02G 15/02* (2013.01)

(58) Field of Classification Search
CPC .. H02G 3/0691; H02G 3/0675; H02G 3/0666; H02G 3/0616; H02G 15/02; H02G 15/007; H02G 15/013; H01B 17/58; B33Y 80/00
See application file for complete search history.

(56) References Cited

U.S. PATENT DOCUMENTS

| | | | | |
|---|---|---|---|---|
| 4,515,991 A | * | 5/1985 | Hutchison | H02G 15/04 29/858 |
| 4,549,037 A | * | 10/1985 | Bawa | H02G 3/088 174/667 |

(Continued)

FOREIGN PATENT DOCUMENTS

| | | |
|---|---|---|
| GB | 2214728 A | 9/1989 |
| WO | WO202000272 A1 | 1/2020 |

OTHER PUBLICATIONS

International Search Report and Written Opinion from corresponding PCT Application No. PCT/EP2021/025514, Mar. 30, 2022, 18 pages, The Netherlands.

*Primary Examiner* — William H. Mayo, III
*Assistant Examiner* — Rhadames Alonzo Miller
(74) *Attorney, Agent, or Firm* — Stinson LLP (57) ABSTRACT

A union body for a cable gland includes a body having a generally cylindrical shape defining an interior surface and a passage extending though the body from a first end to a second end of the body. A groove is formed on the interior surface of the body. The groove is configured to mate with an exterior surface of a cable received in the passage of the body.

13 Claims, 7 Drawing Sheets

(56) References Cited

U.S. PATENT DOCUMENTS

| | | | | |
|---|---|---|---|---|
| 5,691,505 | A * | 11/1997 | Norris | H02G 15/04 |
| | | | | 439/98 |
| 6,537,104 | B1 * | 3/2003 | Hagmann | H02G 3/0666 |
| | | | | 439/461 |
| 6,809,263 | B2 * | 10/2004 | Jackson | H02G 3/065 |
| | | | | 174/651 |
| 6,812,406 | B2 * | 11/2004 | Hand | H02G 15/04 |
| | | | | 174/667 |
| 7,563,993 | B2 * | 7/2009 | Drotleff | H02G 15/007 |
| | | | | 174/653 |
| 7,749,021 | B2 * | 7/2010 | Brodeur | H01R 13/59 |
| | | | | 174/359 |
| 7,781,685 | B2 * | 8/2010 | Bartholoma | H02G 15/04 |
| | | | | 174/654 |
| 10,637,176 | B1 * | 4/2020 | Campbell | H01R 13/5816 |
| 2015/0222107 | A1 * | 8/2015 | Jackson | H02G 15/046 |
| | | | | 174/142 |
| 2017/0059795 | A1 * | 3/2017 | Camarda | H05K 5/06 |
| 2017/0261709 | A1 * | 9/2017 | Camarda | H02G 3/22 |
| 2018/0128400 | A1 * | 5/2018 | Twelves | H02G 15/013 |
| 2018/0301885 | A1 * | 10/2018 | Jackson | H02G 3/0666 |
| 2020/0144799 | A1 * | 5/2020 | Lakerdas | H02G 3/0437 |
| 2021/0344132 | A1 * | 11/2021 | Pavlovic | H01R 13/2407 |

* cited by examiner

ADDITIVELY MANUFACTURED CABLE GLAND

CROSS-REFERENCE TO RELATED APPLICATION

This application claims priority to U.S. Provisional Patent Application Ser. No. 63/131,866, filed Dec. 30, 2020, and which is hereby incorporated by reference in its entirety.

FIELD OF THE DISCLOSURE

The present disclosure generally relates to a cable gland and more particularly to a cable gland having one or more components produced by additive manufacturing.

BACKGROUND OF THE DISCLOSURE

Figure 1A:
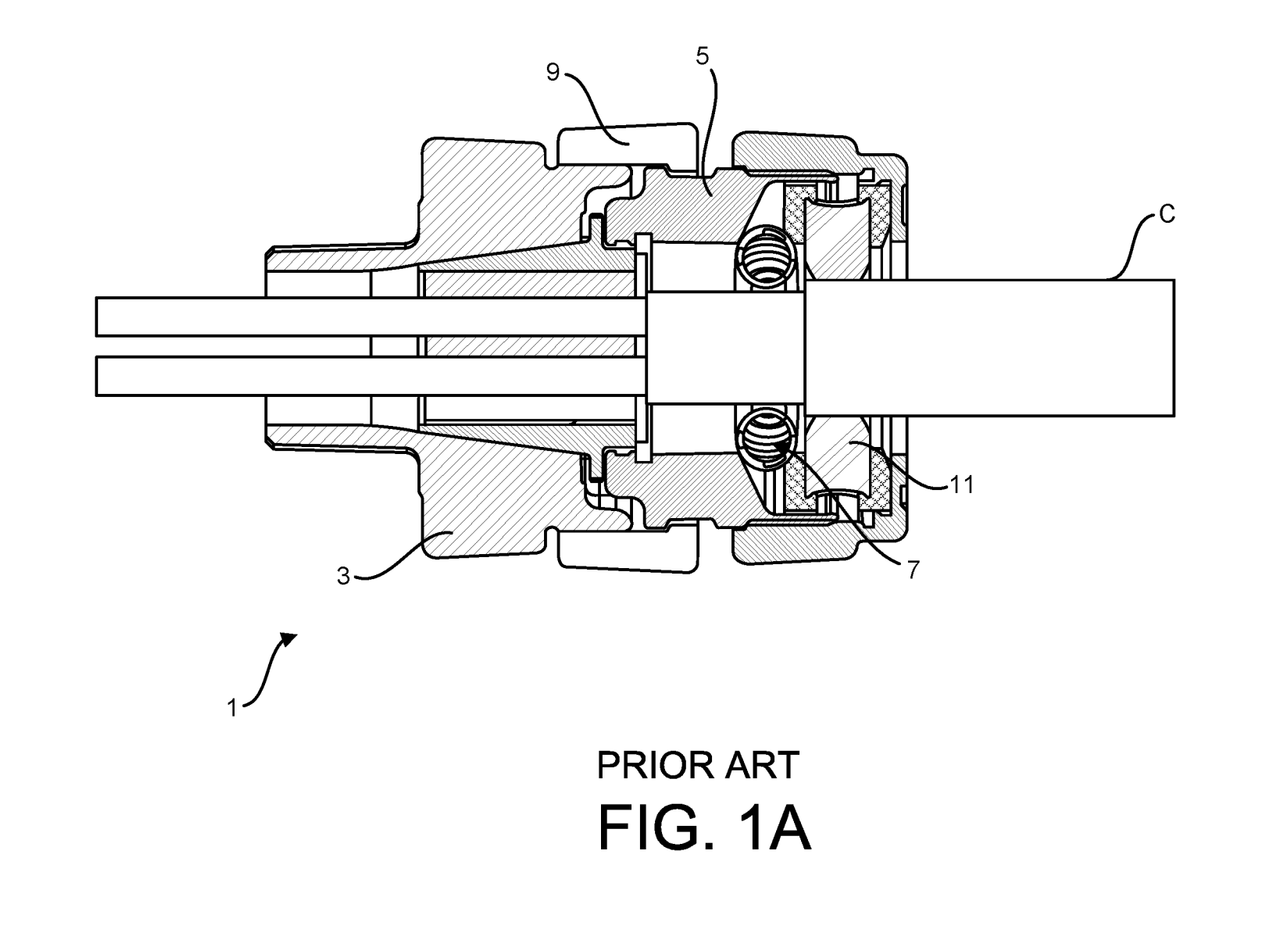
FIG. 1A is a cross section of a cable gland of the prior art and an illustration of a cable received in the cable gland.
Figure 1B:
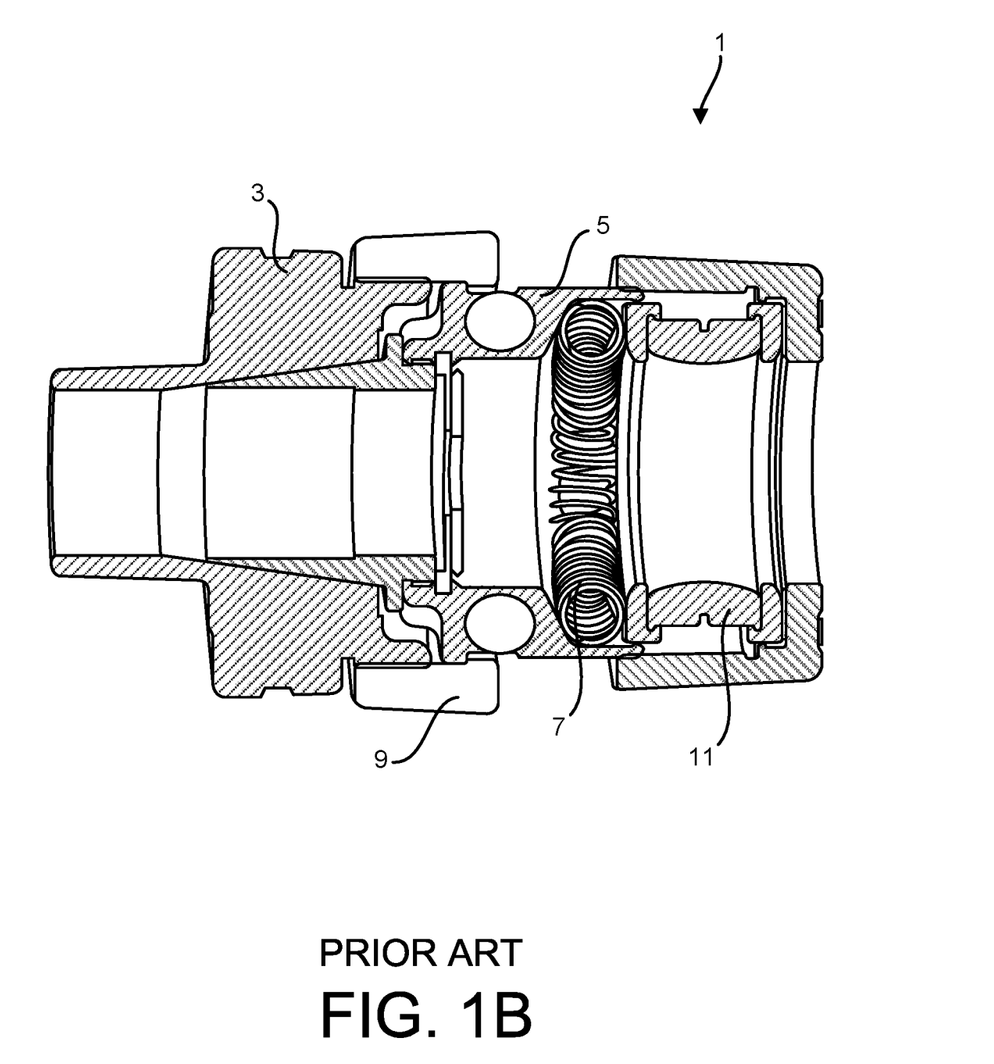
FIG. 1B is a cross section of the cable gland of the prior art.

Cable glands are used for terminating cable in hazardous and nonhazardous environments. More specifically, cable glands generally provide a means for terminating cables, such as unarmored cables (e.g., TC-type) and armored cables, at junction boxes, control centers, panelboards, enclosures, and the like. Typical cable glands are used to seal the junction between a cable and a device and/or an enclosure into which the cable is extending. Referring to FIGS. 1A and 1B, conventional cable glands 1 may comprise at least four components including a hub body 3 for interfacing with the device/enclosure, a union body 5 securable to the hub body and for compressing interior components (e.g., garter spring 7) around the cable C, a gland nut 9 for securing the union body to the hub body, and a bushing 11 received in the union body that seals around and grips the cable for sealing the interior of the gland from the environment. For example, the bushing 11 may seal around a jacket or outer insulation of the cable C.

SUMMARY

In one aspect, a union body for a cable gland generally comprises a body having a generally cylindrical shape defining an interior surface and a passage extending though the body from a first end to a second end of the body. A groove is formed on the interior surface of the body. The groove is configured to mate with an exterior surface of a cable received in the passage of the body.

In another aspect, a cable gland consisting essentially of a hub body having a first end portion and a second end portion opposite the first end portion. The first end portion is configured for connection to a device or enclosure. A union body has a first end portion and a second end portion opposite the first end portion of the union body. The first end portion of the union body is configured for receipt in the second end portion of the hub body. The union body is configured to receive and secure a cable within an internal passage in the union body. A gland nut is configured to be received around and engageable with the union body and the second end portion of the hub body to secure the union body to the hub body.

In yet another aspect, a method of making a union body for a cable gland generally comprises additively manufacturing the union body such that the union body is free of internal or external supports.

DETAILED DESCRIPTION OF THE DISCLOSURE

Figure 2:
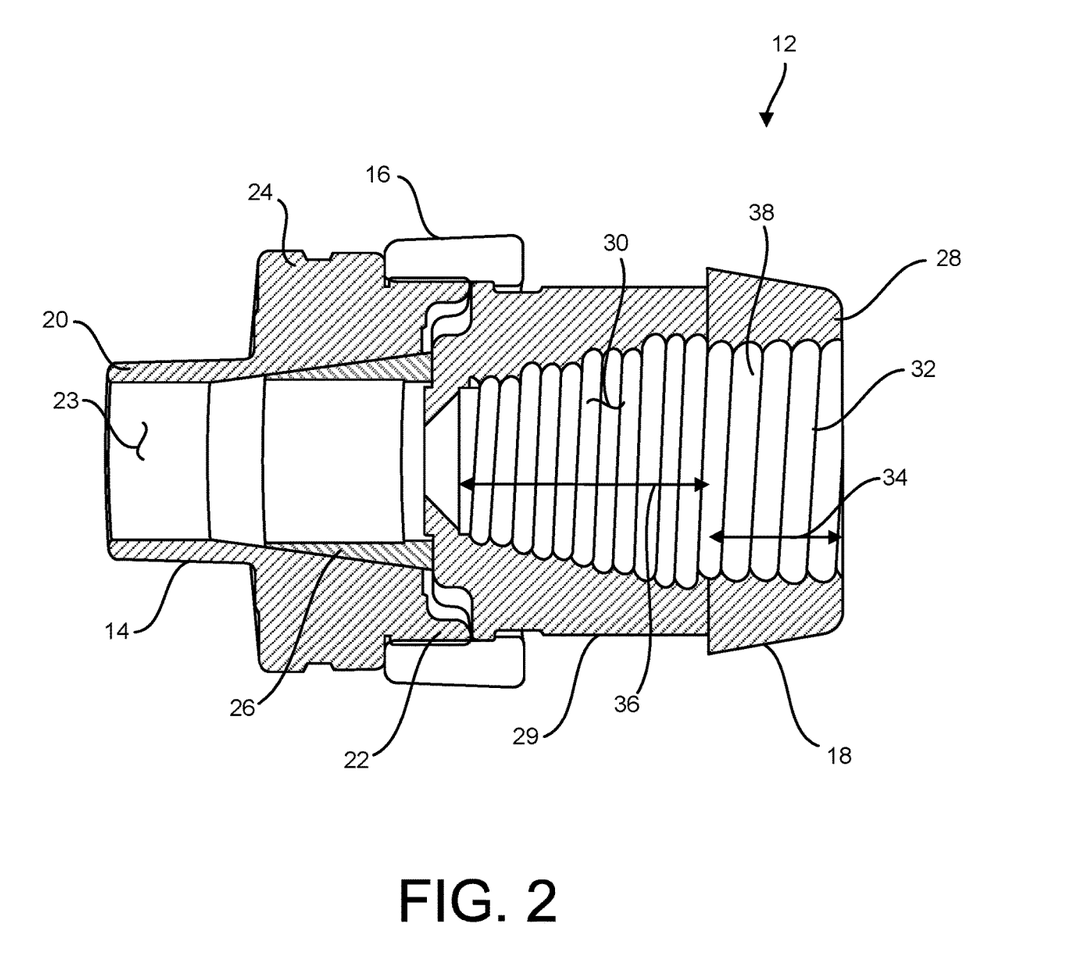
FIG. 2 is a longitudinal section of a cable gland of the present disclosure.

Referring to FIG. 2, an illustrated embodiment of a cable gland constructed according to the teachings of the present disclosure is generally indicated at reference numeral 12. In general, the cable gland 12 is configured to seal the junction between a cable and a device and/or an enclosure into which the cable is extending. As explained in more detail below, the cable gland 12 includes at least one additively manufactured component configuring the gland to be constructed with less total components than conventional cable glands. As a result, the cable gland 12 can be produced more efficiently, and can be customized to a specific cable size and dimension. This can also reduce the overall size and weight of the cable gland 12 thus making the cable gland more cost effective to produce. The other components of the cable gland 12, also described below, are illustrative and may be of other designs or constructions.

Many components of the cable gland 12 may be referred to or shown as having generally cylindrically, circular, annular, or conical features, and as having cylindrical or circular holes, cavities, and openings. Such features may be referred to, or defined by, a circumference, radius, external surface, internal surface, and/or other terms appropriate for defining such features. It should be noted that such features may alternatively be elliptical, polygonal, and the like. As used herein, the terms "axial" and "longitudinal" refer to directions and orientations, which extend substantially parallel to a centerline of the cable gland 12. Moreover, the terms "radial" and "radially" refer to directions and orientations, which extend substantially perpendicular to the centerline of the cable gland 12. In addition, as used herein, the terms "circumferential" and "circumferentially" refer to directions and orientations, which extend arcuately about the centerline of the cable gland.

As described herein, a cable used with the cable gland 12 may be an armored cable that includes an outer jacket layer, an armor layer, and at least one conductor. The cable may alternatively be an unarmored cable that includes an outer jacket layer, an insulation layer, and at least one conductor. It should also be appreciated that the cable gland 12 may be used with any other cable layer configuration that enables the assembly to function as described herein.

In general, and with reference to FIG. 2, the cable gland 12 includes a hub body, generally indicated at reference numeral 14, a gland nut, generally indicated at reference numeral 16, and a union body, generally indicated at 18. Together, the hub body 14 and the union body 18 define a gland body. In one embodiment, the hub body 14 has a first end portion 20 with external connection thread(s) (not shown) for threading into a device, an enclosure, or other structure, and a second end portion 22 with an external nut thread (not shown) for threadably mating with the gland nut 16. An internal passage 23 extends through the first and second ends 20, 22 of the hub body 14. The hub body 14 may comprise or be formed from, for example, a metal, such as aluminum, stainless steel, and/or brass. A face seal (not shown) and a locknut (not shown) may be received on the first end 20 of the hub body 14. As installed, the face seal is sandwiched between an exterior face of the device, enclosure, or other structure and a tool coupling portion 24 (e.g., a hexagonal or other polygonal structure) to create the watertight seal and inhibit ingress of water, oil, and/or other debris into the device, enclosure, or other structure. The face seal may comprise or be formed from, for example, silicone, such as a silicone rubber having a durometer of 70 Shore A Hardness. The locknut is threaded on the connection thread on the first end 20 of the hub body 14 within the device, enclosure, or other structure and contacts the interior face of the device, enclosure, or other structure to lock the cable gland 10 to the device, enclosure, or other structure. The locknut may comprise or be formed from, for example, a metal, such as aluminum, stainless steel, and/or brass. In one or more embodiments, the face seal and/or the locknut may be omitted. As will be explained in greater detail below, the annular grounding spring (e.g., garter spring) has been omitted. In conventional cable glands, the grounding spring engages and surrounds the cable armor to create a grounding connection. However, in the current design the union body 18 itself provides the grounding function of the garter spring.

Referring to FIGS. 2-5, the union body 18 comprises a generally cylindrical body defining an internal passage 30 extending through first and second end portions 26, 28 of the union body. A middle section 29 extends between the first and second end portions 26, 28 of the union body 18. The internal passages 30, 23 of the union body 18 and the hub body 14 are generally alignable with one another when the union body is attached to the hub body to form an internal passage of the gland body that is configured to receive the cable. The first end portion 26 of the union body 18 has a tapered exterior profile defining a generally conical shape configured to be received in the correspondingly shaped interior of the second end 22 of the hub body 14, as shown in FIG. 2. The internal passage 30 of the union body 18 is defined, at least partially, by an interior surface 32 of the union body. An inner cross-sectional dimension (i.e., diameter) of the internal passage 30 generally tapers from the second end portion 28 of the union body 18 toward the first end portion 26. As shown, as first section 34 of the passage 30 extending along the second end 28 portion has a generally constant inner cross-sectional dimension. In one embodiment, the inner cross-sectional dimension of the union body 18 at the first section 34 is between about 6 inches and about 3 inches. A second section 36 extends from the first section 34 toward the first end portion 26 of the union body 18 and has a tapering inner cross-sectional dimension that tapers from an end of the second section adjacent the first section 34 to an opposite end. The second section 36 is generally disposed in the middle section 29 of the union body 18. In one embodiment, the inner cross-sectional dimension of the union body 18 at the second section 36 tapers from between about 3 inches and about 4 inches at the end adjacent the first section 34 to between about 0.4 inches and about 1 inch at the opposite end. In one embodiment, the inner cross-sectional dimension at the second section 36 tapers at an angle of between about 5 and about 45 degrees. The union body 18 may comprise or be formed from, for example, a metal, such as aluminum, stainless steel, and/or brass. The dimensions and interior profile of the union body 18 may also be other than described.

Figure 3:
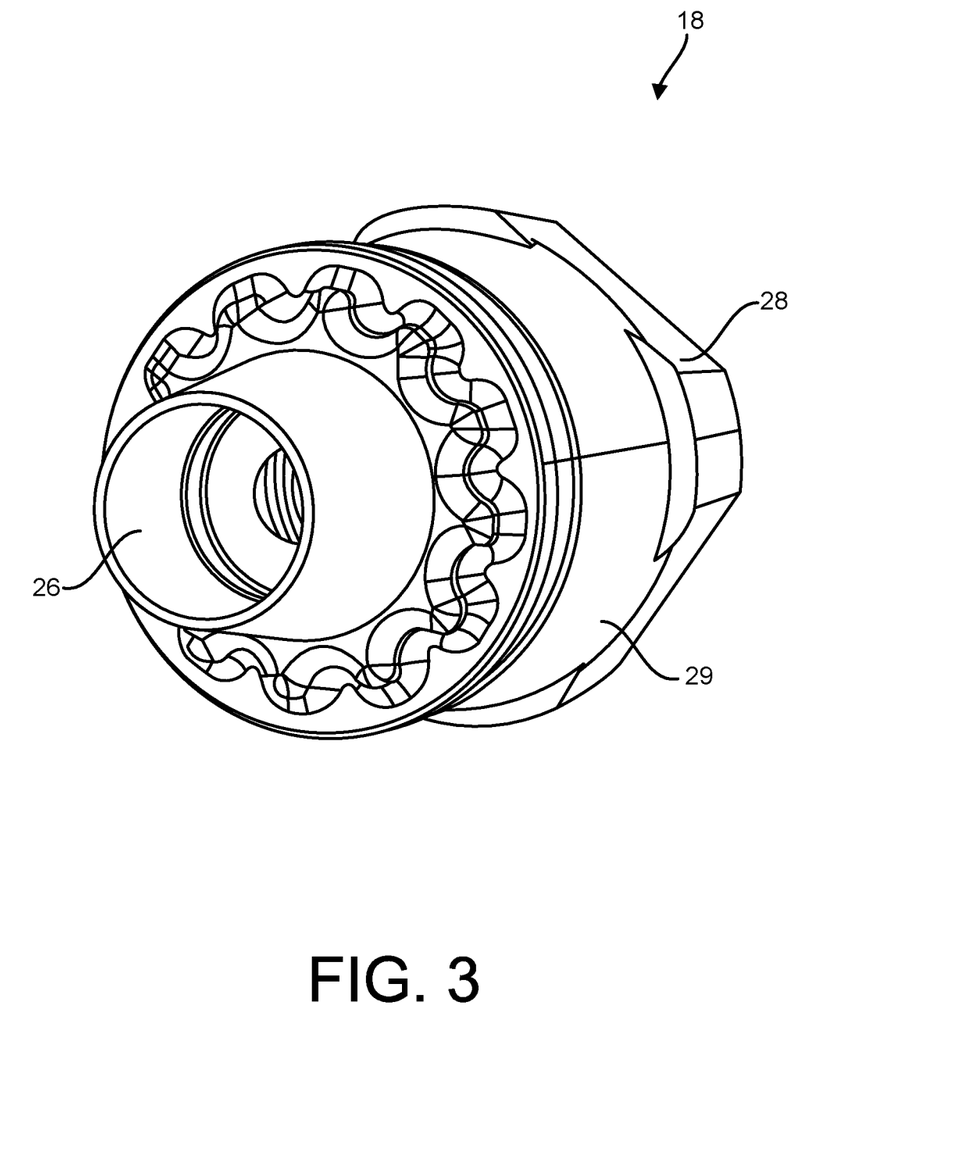
FIG. 3 is a perspective of a union body of the cable gland in FIG. 2.
Figure 4:
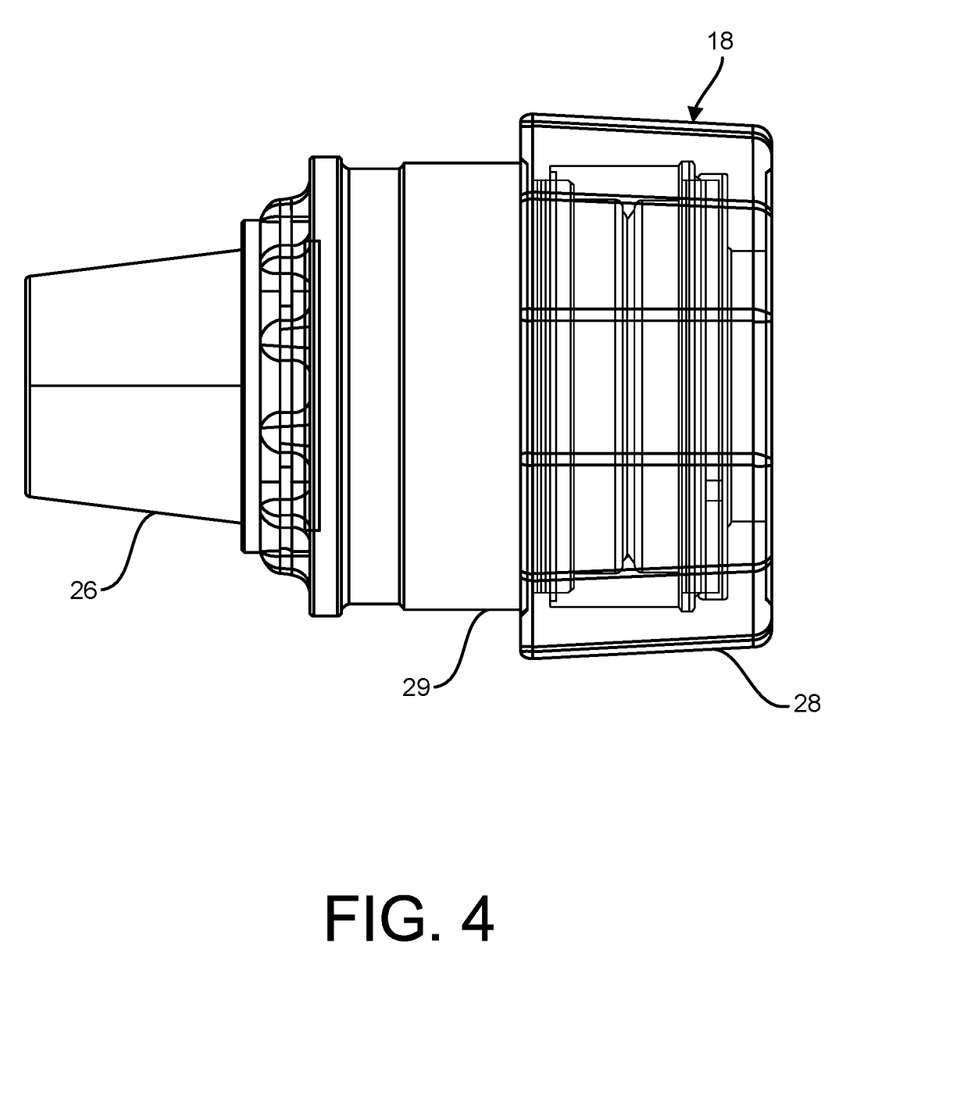
FIG. 4 is a side view of the union body.
Figure 5:
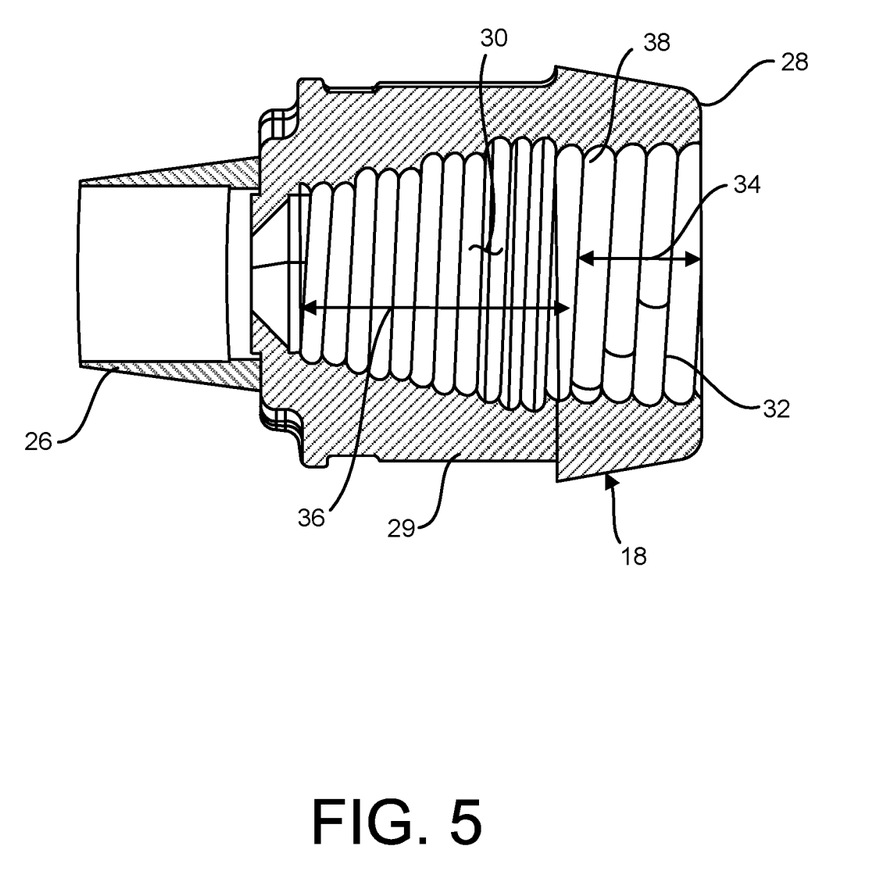
FIG. 5 is a longitudinal section of the union body.

In the illustrated embodiment, the interior surface 32 also comprises a spiral groove 38 extending circumferentially around and longitudinally along the interior surface. The spiral groove 38 is generally disposed in the second end portion 28 and middle section 29 of the union body 18. In the illustrated embodiment, the spiral groove 38 is not disposed in the first end portion 26 of the union body 18. The groove 38 forms a rounded recess in the interior surface 32 whereby a cross-section of a single segment (i.e., a single diametrically extending portion) has a generally U-shape. Additionally, a pitch of the spiral groove 38 may be between about 0 and about 80 degrees. It will be understood that the spiral groove 38 and profile of the interior surface 32 may have other configurations without departing from the scope of the disclosure.

The spiral groove 38 provides a grip texture on the interior surface 32 for holding the cable within the internal passage 30. In one embodiment, the tapering profile of the interior surface 32 alone, and in combination with the spiral groove 38, has a configuration designed to accommodate a relatively wide range of cable sizes (i.e., outer diameter sizes). For instance, cables having outer diameters between about 2 inches and about 2.7 inches may be suitably received in and secured to the cable gland 12 by friction fit. The spiral groove 38 may also provide a further gripping means by generally conforming to the external spiral configuration of the cable received in the cable gland 12. In another embodiment, the spiral groove 38 may be specifically configured to have a mating spiral configuration with the external surface of cable being received in the cable gland 12. In this instance, the cable gland 12 would be uniquely configured for use with a specific cable. Thus, the inner cross-sectional dimensions along the first and second sections 34, 36 would be sized and shaped to match the outer cross-sectional dimensions of the portions of the cable received in the union body 18 (i.e., diameters of the spiral/conical portions of the cable).

The union body 18 may be manufactured by any suitable means. In one embodiment, the union body 18 is manufactured by additive manufacturing. For example, the union body 18 may be 3D printed using standard 3D printing technology. Therefore, the union body 18 can be manufactured without any internal or external supports, thus reducing the post processing steps. The additively manufactured union body 18 can also be customized to fit the unique construction of the cable with which it will be used. In particular, the union body 18 can be printed such that the interior surface 32 is a negative of the cable profile. This customization reduces the size and weight of the cable gland 12, by reducing the length and diameter of the union body 18, making it cheaper to produce and easier to use. Additionally, a lattice structure can be incorporated into the union body 18 to reduce weight of the union body, thus reducing the total weight and cost of the cable gland 12. In one embodiment, customization can be integrated with an automated design process where the design is modified based on a customer's inputs of the specifications of the cable. The union body 18 can then be printed and delivered to the customer. This process can be completed within one to two weeks whereas conventional cable glands can take over a month for production and distribution.

It will be understood that in the previously discussed embodiment, the union body 18 is produced by additive manufacturing while the hub body 14 and gland nut 16 may be stock components having conventional configurations. However, it is further envisioned to also produce the hub body 14 and gland nut 16 by additive manufacturing. In this embodiment, the entire cable gland 12 is produced by additive manufacturing and therefore the entire cable gland can be sized and shaped to fit its desired use. Still other combinations in the cable gland 12 of stock and additively manufactured components are envisioned.

Further, the additively manufactured cable gland 12 allows for a reduction in the total number of components of the cable gland. In the illustrated embodiment, the cable gland 12 consists essentially of the hub body 14, gland nut 16 and union body 18. Thus, the cable gland 12 is constructed using only three total components. This allows for the omission of conventionally used internal components such as grounding springs, sleeves, bushings, and washers. Instead, the union body 18 is constructed to provide the functionality of these internal components in one single unitary component. In particular, the direct metal-to-metal contact between the interior surface 32 of the union body 18 and the exterior surface (i.e., armor) of the cable provides the grounding function of conventional grounding springs. Additionally, the tapered interior surface 32 and spiral groove 38 provide the sealing engagement with the cable and radial compression on the cable that is provided with conventional springs, sleeves, and bushings. For example, the armor on the cable is locked in place within the second section 36 of the union body 18, and the outer insulation on the cable is engaged and locked in place within the first section 34 of the union body. So the union body 18 seals around the jacket (e.g., PVC jacket) of the cable. Accordingly, the sealing and retaining function of conventional separate internal components are replaced with the internal construction of the union body 18. As a result, common seal wear and tear that occurs on conventional cable glands is eliminated. This in-turn reduces the maintenance cost of the cable gland 12. The construction of the union body 18 also eliminates the need to use the gland nut 16 to apply force to the other components of the cable gland 12 to clamp around the cable. Instead, the gland nut 16 is used primarily to secure the union body 18 to the hub body 14 and thereby couple the cable to the enclosure/device. The clamping force exerted on the cable is produced exclusively by the construction of the union body 18. In one example, the union body 18 is suitable for a cable gland that is rated as IP66 under International Protection Marking and/or rated NEMA 4X under the National Electrical Manufacturer Association.

Figure 6:
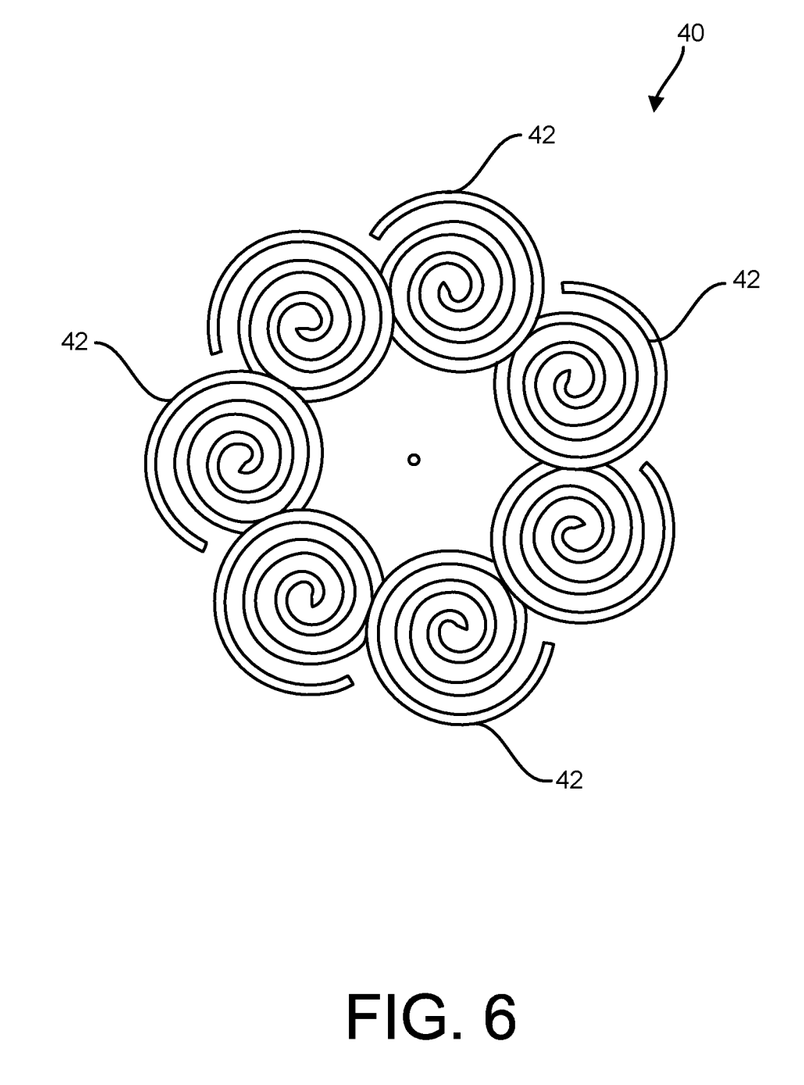
FIG. 6 is an illustration of a garter spring of the cable gland.

Additionally, a spring 40 (FIG. 6) maybe disposed (e.g., formed on) the interior surface 32 of the union body 18. For example, if additional compression force is required, such as for cable glands used in hazardous locations, the spring can be included on the union body 18. Thus, the spring 40 may function like a conventional garter spring. The spring 40 can also be produced by additive manufacturing whereby the spring is formed during the formation process of the union body 18. Therefore, the spring 40 will be fixed to the interior surface 32 of the union body 18 and form part of the union body. In the illustrated embodiment, the spring 40 comprises a plurality of discrete spring elements 42 configured to be disposed circumferentially around the interior surface 32 of the union body 18. The discrete spring elements 42 are linked together so that they function as one spring to provide the radial force on the cable when the cable is received in the union body 18. Still other configurations of the spring 40 are envisioned without departing from the scope of the disclosure.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A union body for a cable gland, the union body comprising:
    a body having a generally cylindrical shape defining an interior surface and a passage defined by the body and extending though the body from a first end to a second end of the body, wherein the body includes a first end portion for being received in a hub body of the cable gland, a second end portion opposite the first end portion, and a middle section between the first and second end portions; and
    a spiral groove formed on the interior surface of the body, wherein the spiral groove is disposed on the interior surface at the second end portion and middle section of the body of the union body,
    wherein the spiral groove at the middle section of the body is configured to mate with an exterior surface of a non-jacketed armored portion of a cable received in the passage of the body, wherein a cross-sectional dimension of the passage defined by the spiral groove at the middle section of the body generally tapers along a length of the body,
    wherein the spiral groove at the second portion of the body is configured to mate with an exterior surface of a jacketed armored portion of the cable received in the passage of the body,
    wherein the body including the groove formed in the body is made of metal.

2. The union body set forth in claim 1, wherein the union body is formed by additive manufacturing.

3. The union body set forth in claim 2, wherein the spiral groove is rounded.

4. The union body set forth in claim 1, further comprising a spring disposed in the interior passage of the body, wherein the body and spring are integrally formed as a single, monolithic structure.

5. The union body set forth in claim 4, wherein the body and spring are formed by additive manufacturing such that the spring is fixed to the body.

6. A method of making the union body set forth in claim 1, the method comprising additively manufacturing the union body such that the union body is free of internal or external supports.

7. The method set forth in claim 6, wherein the union body is made of metal.

8. The method set forth in claim 6, further comprising forming a spring on the interior surface of the union body during the process of additively manufacturing the union body.

9. The union body set forth in claim 1, wherein the groove extends to an end of the body.

10. A cable gland consisting essentially of:
a hub body having a first end portion and a second end portion opposite the first end portion, the first end portion being configured for connection to a device or enclosure;
a union body having a first end portion, a second end portion opposite the first end portion of the union body, and a middle section between the first and second end portions, the first end portion of the union body being configured for receipt in the second end portion of the hub body, the union body being configured to receive and secure a cable within an internal passage in the union body defined by the union body, a spiral groove being formed on an interior surface of the union body, wherein the spiral groove is disposed on the interior surface at the second end portion and middle section of the union body, the spiral groove at the middle section of the union body being configured to mate with an exterior surface of a non-jacketed armored portion of a cable received in the internal passage, a cross-sectional dimension of the internal passage defined by the spiral groove at the middle section of the union body generally tapering along a length of the union body, wherein the spiral groove at the second portion of the union body is configured to mate with an exterior surface of a jacketed armored portion of the cable received in the passage of the union body; and
a gland nut configured to be received around and engageable with the union body and the second end portion of the hub body to secure the union body to the hub body, wherein the cable gland is free of a bushing or sleeve disposed in the cable gland.

11. The cable gland set forth in claim 10, wherein the union body is formed by additive manufacturing.

12. A union body for a cable gland, the union body comprising:
a body having a generally cylindrical shape defining an interior surface and a passage defined by the body and extending though the body from a first end to a second end of the body, wherein the body includes a first end portion for being received in a hub body of the cable gland, a second end portion opposite the first end portion, and a middle section between the first and second end portions; and
a spiral groove formed on the interior surface of the body,
wherein the spiral groove is disposed on the interior surface at the second end portion and middle section of the body of the union body,
wherein the spiral groove at the middle section of the body is configured to mate with an exterior surface of a non-jacketed armored portion of a cable received in the passage of the body,
wherein the spiral groove at the second portion of the body is configured to mate with an exterior surface of a jacketed armored portion of the cable received in the passage of the body,
wherein the body including the groove formed in the body is made of metal.

13. The union body set forth in claim 12, wherein a width of the groove at the second portion of the body is greater than a width of the groove at the middle portion of the body.

* * * * *